United States Patent [19]

Pannu

[11] Patent Number: 4,666,444
[45] Date of Patent: May 19, 1987

[54] EASILY INSERTABLE INTRAOCULAR LENS

[76] Inventor: Jaswant S. Pannu, 4850 W. Oakland Blvd., Lauderdale Lakes, Fla. 33313

[21] Appl. No.: 775,831

[22] Filed: Sep. 13, 1985

[51] Int. Cl.⁴ ............................................. A61F 2/16
[52] U.S. Cl. ...................................................... 623/6
[58] Field of Search ............................................ 623/6

[56] References Cited

U.S. PATENT DOCUMENTS

| 4,249,271 | 2/1981 | Poler | 623/6 |
|---|---|---|---|
| 4,403,354 | 9/1983 | Rainin | 623/6 |
| 4,426,741 | 1/1984 | Bittner | 623/6 |
| 4,435,855 | 3/1984 | Pannu | 623/6 |
| 4,513,456 | 4/1985 | White | 623/6 |
| 4,527,294 | 2/1985 | Heslin | 623/6 |
| 4,576,607 | 3/1986 | Kelman | 623/6 |
| 4,585,454 | 4/1986 | Fabricant | 623/6 |
| 4,615,701 | 10/1986 | Woods | 623/6 |

OTHER PUBLICATIONS

Lens Styles from Cilco (Advertisement Brochure from Cilco 6 pages) pp. 1, 4 & 6, cited, Styles SK-1, SK-2, and SK-4 on p. 4 Relied upon, Oct. 1982.
Copeland IntraLenses, Inc. Advertisement.
Ocular Surgery News, Buyers Guide, Aug. 1, 1985, vol. 3, No. 15.

*Primary Examiner*—Ronald L. Frinks
*Attorney, Agent, or Firm*—Banner, Birch, McKie & Beckett

[57] ABSTRACT

The present invention is directed to an easily insertable intraocular lens including attachment means of various types disposed on the lens body for connecting the haptic to the lens body during insertion of the lens into the eye, thus reducing the overall radial extend of the lens. The haptic may have a snag-resistant loop which is held by the attachment means or a second attachment means which connects to the first. The lens also may have a haptic made from at least two different materials.

5 Claims, 15 Drawing Figures

EASILY INSERTABLE INTRAOCULAR LENS

TECHNICAL FIELD

The present invention relates to a one-piece, two-piece, or multiple piece intraocular lens and, more particularly, to an easily insertable intraocular lens.

BACKGROUND OF THE INVENTION

When the lens or lens nucleus is removed from the eye during cataract surgery, it is common to replace the lens with an intraocular lens implant. Intraocular lenses are optical implants for the replacement of the human lens in the visual correction of aphakia. Intraocular lens implants generally include a circular optical portion and one or more support structures extending outwardly from the optical portion, known as the haptics. The haptics support and fix the lens in position once the lens is inserted. Such intraocular lenses may be inserted either in the anterior chamber or posterior chamber of the eye following either intracapsular or extracapsular cataract extraction. However, the preferred location for the lens of the present invention is the capsular bag in the posterior chamber with the optic portion of the lens centered under the pupil. The preferred surgical technique is extracapsular cataract extraction.

Although the haptics are essential for supporting and positioning the lens once it is inserted in the eye, they make the lens more difficult to insert into the small and delicate eye chambers. The large and cumbersome haptics projecting from the optical portion are very difficult to maneuver. To eliminate this problem, surgeons in the past have tied the haptics together with a stitch of thread, pulling the haptics inwardly toward the lens body, as disclosed in U.S. Pat. No. 4,249,271. Thus, the lens is easier to insert due to its reduced span. However, the stitch may be easily broken during manipulation of the lens, resulting in an even greater chance of injury as the haptics snap outwardly. Moreover, it may be unnecessarily time consuming and difficult for the surgeon to properly stitch the haptics together. Additonally, it is necessary to insert a sharp surgical scalpel into the eye chamber after the lens is inserted to cut the stitch and release the haptic. This can be a dangerous and difficult procedure. In more conventional insertion techniques with a forcep, almost all manipulation of the lens takes place outside the eye chamber.

Other intraocular lenses, such as the Woods lens marketed by Copeland Intra Lenses, Inc., have used hooked haptics which hook to apertures in the optic portion of the lens. This also is unsatisfactory in that the hooked haptic can be easily displaced during lens insertion causing eye tissue trauma. Moreover, the hooked haptic has a relatively sharp, pointed end which can damage eye tissue.

SUMMARY OF THE INVENTION

The present invention overcomes these disadvantages by providing attachment means, such as a flange, flap, aperture, button, groove or the like to which the haptics may be easily, quickly, and positively attached for insertion. Thus, the haptics may be securely held inwardly toward the lens body providing a reduced diameter lens which is easier to insert than conventional intraocular lenses. Moreover, the haptics are securely fastened to the optical portion of the lens to prevent inadvertent release during lens insertion. Once the lens is inserted, however, the haptics can be readily displaced into their expanded position with little additional manipulation.

The present invention is a one-piece, two-piece, or multiple piece intraocular lens which is more easily insertable than conventional intraocular lenses. The invention comprises a lens body including an optic portion. The lens has one or more support structures or haptics, extending outwardly from the periphery of the lens body. At least one lens body attachment element is disposed on the lens body. The attachment element may be located either on the surface or on the peripheral edge of the lens body. The end of the haptics may be secured directly to the lens body attachment elements. Alternatively, the haptics may include a haptic attachment element disposed on or near the free ends of the haptics. Thus, the haptics may be drawn in toward the lens body and secured to the lens body by the attachment elements, conveniently and efficiently reducing the radial extent of the haptics and facilitating lens insertion. Once the lens is positioned in the eye chamber, the haptics may be readily detached from the lens body and positioned within the eye chamber to properly support the lens.

The present invention also uses a novel two-part haptic structure to improve flexibility of the haptics and to make the haptics less irritating. Most two-piece intraocular lenses use a haptic made from a polypropylene fiber marketed as Prolene. Although very flexible, Prolene may cause some irritation to eye tissues. Most one-piece lenses are made from polymethylmethacrylate (PMMA). However, PMMA haptics are not as flexible as those made from Prolene. The two-part haptic of the present invention includes a first, inner part, adjacent the optical portion, made from Prolene or a similar material and a second, outer part integral with the first part, made from PMMA or a similar material. Additionally, more than two materials may be combined to achieve the desired degree of flexibility and comfort.

DETAILED DESCRIPTION OF THE INVENTION

Figure 1:
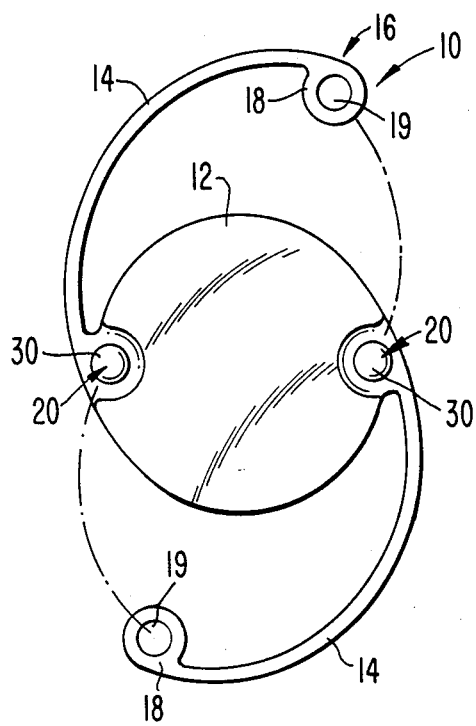
FIG. 1 is a plan view of an intraocular lens according to one embodiment of the invention, with the lens in the open position.

In FIG. 1 is illustrated an intraocular lens in accordance with the proposed invention and generally designated as 10. The lens 10 comprises lens body 12 having an optical portion and preferably two outwardly extending support structures, or haptics, 14. However, the number of haptics is not critical to the invention and could vary with particular lens designs. Haptics 14 may be integrally formed with lens body 12, as shown in the drawings, forming a one-piece lens. Alternatively, haptics 14 may be separate elements which are attached to lens body 12, as is well-known in the art, forming a two-piece or multiple piece lens. Although haptics 14 are shown having a smooth, continuously curved contour, they may have any contour, including an irregular contour, as is well-known in the art. Lens body 12 may be made from any material which can provide the required optical correction and will be non-reactive with human tissue, such as polymethylmethacrylate (PMMA). Haptics 14 may be made from PMMA, a commonly used polypropylene fiber marketed as Prolene, a combination of these two or similar materials, or a combination of more than two materials as more fully described in conjunction with FIG. 14.

Preferably, the free end 16 of haptic 14 includes snag-resistant means 18 formed of an uninterrupted continuously smoothly curved open loop, as shown generally in applicant's U.S. Pat. No. 4,435,855, although other loop configurations may be used. Loop 18 preferably has an outer diameter of approximately 1.5 mm. and a central aperture 19 formed therein. At least one attachment means 20 is disposed on the lens body. As further described below, the attachement means may be a flange, aperture, button, groove or any other element or structure capable of removably connecting haptics 14 to lens body 12. The number of attachment means 20 preferably corresponds to the number of haptics 14, but it may be desirable in certain constructions to draw only one of several haptics towards the lens body. Before insertion, the surgeon secures loop 18 to the attachment means 20, as shown, for example, in FIGS. 2, 6 and 7, thereby drawing the haptic 14 inwardly toward the lens body 12 and reducing the overall radial extent of lens 10. Additionally, haptic 14, with or without loop 18, may have a second attachment means 22, such as a flange, button, aperture, groove or similar structure, as shown, for example, generally in FIG. 7, for connecting with attachment means 20 during insertion of the lens into the eye. Second attachment means 22 has a complementary shape with respect to attachment means 20, so that the first attachment means may be securely connected to the second attachment means. Once the lens is properly positioned within the eye, the haptic is released and secured in a manner conventional in the art.

Figure 2:
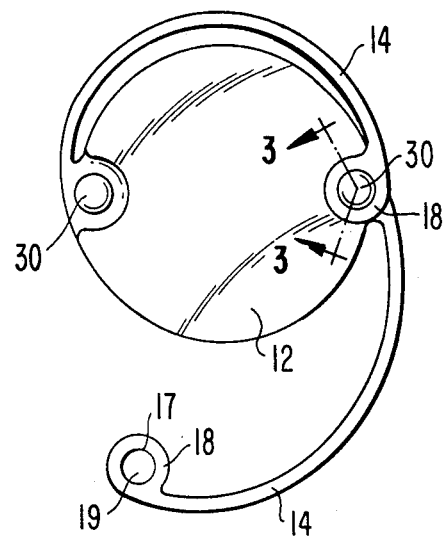
FIG. 2 is a plan view of the lens shown in FIG. 1 with the lens in the closed position.
Figure 3:
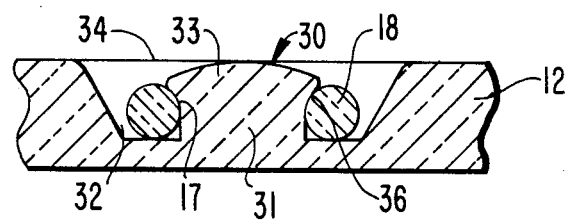
FIG. 3 is a sectional view along line 3—3 of FIG. 2.

FIGS. 1-3 illustrate one specific preferred embodiment of the present invention. In FIGS. 1-3 attachment means 20 comprises a button 30 disposed in a shallow well 32 on lens body 12. Preferably wells 32 are positioned approximately 0.3-1.7 mm. inwardly from the periphery of lens body 12. Button 30 includes a stem portion 31 fixed to lens body 12 and a dome-shaped head portion 33. The lens body of a typical intraocular lens is approximately 6-7 mm. in diameter. Each well is preferably 0.5-1.5 mm. in diameter and approximately 0.1 mm. deep. The height of button 30 also is approximately 0.1 mm. Thus, the depth of well 32 and the height of button 30 are such that the button does not extend substantially above the face of the lens body, so that the button does not add measurably to the thickness of the lens or provide a protrusion which could damage the eye. In the embodiment shown in FIGS. 1-3, snag-resistant loop 18 fits over head 33 to demountably couple haptics 14 to lens body 12 during insertion of the lens, thus drawing the haptics toward the lens body providing a lens of reduced diameter or radial extent, as shown in FIGS. 2 and 3. Aperture 19 of loop 18 provides resiliency to loop 18. In this embodiment, however, it also functions as an attaching means for attaching loop 18 to button 30. However, loop 18 may assume other configurations, such as the open loop configurations shown in applicant's U.S. Pat. No. 4,542,541, and still function to couple the haptics and lens body. Dome-shaped head 33 of buttton 30 has snag-resistant sloping shoulders 34 which facilitate easy connection and disconnection of snag-resistant loop 18. Additionally, button 30 has a circumferential groove 36 cut into its periphery to grip the inner edge portion 17 of loop 18 during insertion of the lens into the eye. Again, after insertion, the haptic is readily displaced by the surgeon to assume its proper position in the eye chamber.

Figure 4:
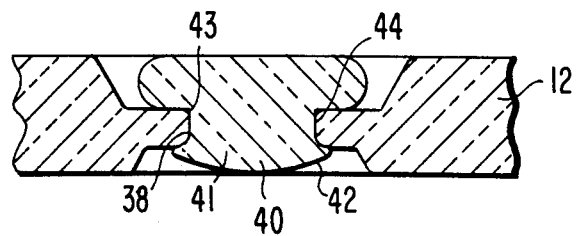
FIG. 4 is a sectional view, similar to FIG. 3, of another embodiment of the invention.
Figure 5:
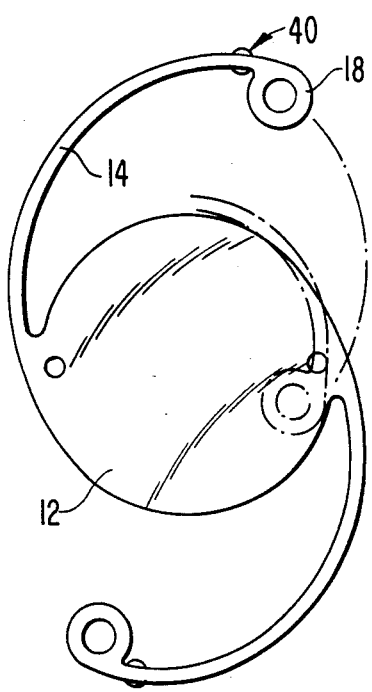
FIG. 5 is a plan view of another embodiment of the invention.

An alternative embodiment is illustrated in FIGS. 4 and 5. For the embodiment shown in FIGS. 4 and 5, the general construction of lens 10 is the same as shown in FIGS. 1-3. However, in FIGS. 4 and 5, a first attachment means comprises an aperture 38 located near the periphery of lens body 12. A second attachment means comprises a button 40 disposed on or adjacent to loop 18. In FIG. 5, button 40 is shown adjacent loop 18, however, this is for purposes of illustration only, since it is within the scope of the invention to position button 40 on loop 18 itself. Button 40 has a crowned head portion 41 with sloping shoulders 42 and a circumferential groove 43 which is engaged by the inner edge 44 of aperture 38. In preparation for insertion of the lens into the eye, the button 40 is fit within aperture 38, thus drawing the haptic inwardly toward the lens body and effectively reducing the overall lens diameter, i.e., optical portion and haptics, during insertion. Once the lens is positioned within the eye, the button 40 is easily displaced from aperture 38, thus extending the haptics so that they can position and support the lens.

Figure 6:
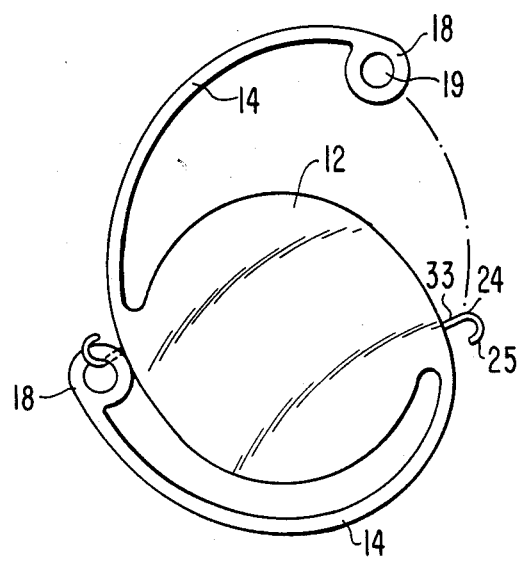
FIG. 6 is a plan view of another embodiment of the invention.
Figure 8:
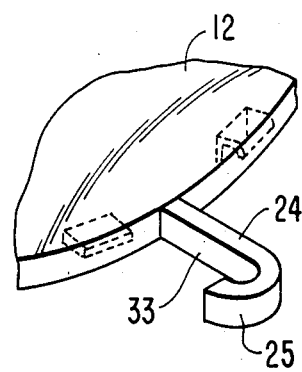
FIG. 8 is a partial perspective view of a detail of the lenses shown in FIGS. 6 and 7.

FIG. 6 illustrates another preferred embodiment of the present invention. Attachment means 20 comprises a flange 24 with a curved outer end 25 forming a relatively broad hook portion. Flange 24 is shown projecting radially from the outer peripheral edge of lens body 12. However, flange 24 may be fixed to the top or underside surface of the optical portion. In this configuration, the stem of flange 24 could project axially from the optical portion, as shown in dotted outline in FIG. 8. A third alternative is to form flange 24 by making a groove in the lens body, as shown in dashed outline in FIG. 8. Flange 24 and hook 25 should be as broad as possible in order to avoid creating a sharp, pointed, projection which can damage eye tissues. Loop 18 on the free end 16 of the haptic 14 is placed over flange 24, as shown in FIG. 6, to securely hold haptic 14 adjacent to lens body 12 during insertion of the lens into the eye. The width of flange 24 is such that it can fit through aperture 19 of loop 18, but once so inserted cannot be displaced except by manipulation by the surgeon.

Figure 7:
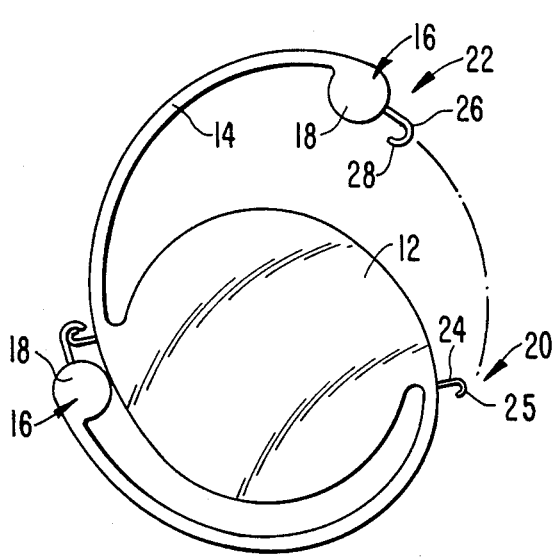
FIG. 7 is a plan view of another embodiment of the invention.

Alternatively, as illustrated in FIG. 7, a second attachment means 22 may be provided on or near free end 16. In FIG. 7, the second attachment means is shown on snag resistant element 18 (aperture 19 has been deleted in this embodiment) but it could also be positioned on haptic 14 adjacent free end 16. Second attachment means 22 comprises a second flange 26 with a curved outer end 28 forming a relatively broad hook portion to flange 24. Flange 26 may also be formed and positioned in the alternative arrangements described above for flange 24. In this way, rather than placing the loop 18 over flange 24, flange 24 is connected to flange 26, thus securing haptic 14 to the lens body 12 during insertion of the lens into the eye. The broad extent of the flanges 24 and 26 provides a significant contact surface area between the flanges and ensures a secure connection between the haptics and lens body. After insertion, flange 24 is readily displaced from flange 26 using any preferred forceps.

Figure 9:
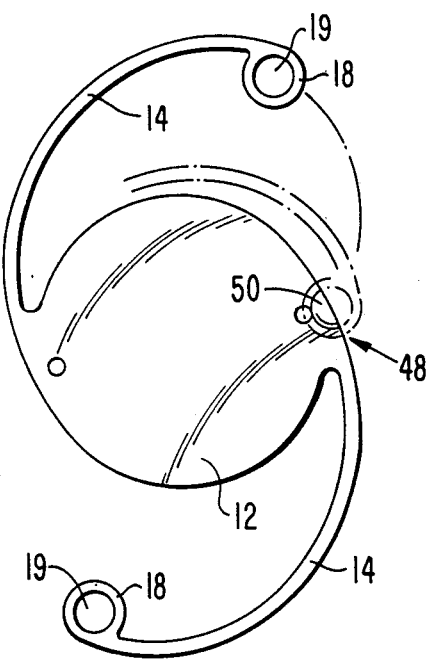
FIG. 9 is a plan view of another embodiment of the invention.
Figure 10:
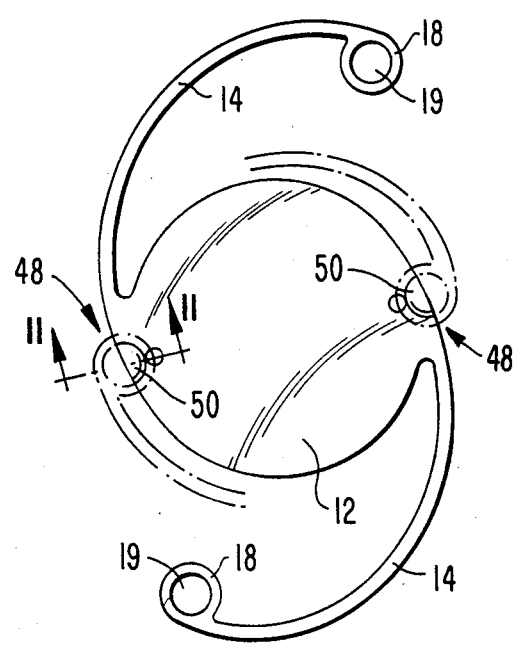
FIG. 10 is a plan view of another embodiment of the invention.
Figure 11:
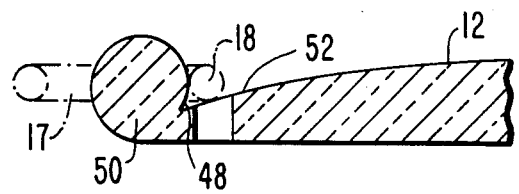
FIG. 11 is a sectional view along line 11—11 of FIG. 10.

FIGS. 9–11 show another embodiment of the invention. Again, the basic construction of lens 10 is as previously described. In FIGS. 9–11, lens body 12 is formed with recessed areas or grooves 48 near its periphery. Groove 48 may be formed by forming an enlarged bulbous ridge 50 on the outer periphery of lens body 12 contiguous to an inwardly sloping or tapered shoulder 52, tapering towards the edge of lens body 12, as shown in FIG. 11. Ridge 50 may project up to the height or thickness of lens body 12 or slightly above it. Additionally, ridge 50 may be formed on either the top side or underside of the lens. Groove 48 may of course be formed in other ways, such as by removing material from lens body 12 to create a channel. In so constructing groove 48, it may be desirable to reinforce the underside of lens 10 with a rib under the channel. The size and depth of the rib would correspond to the size and depth of the channel.

In FIG. 9 only a single groove 48 is shown, whereas in FIG. 10, two such grooves are shown. While it is generally desirable to provide the same number of attachment elements as haptics, in order to provide the most compact lens arrangement, there may be particular lens constructions where only a single attachment means is desirable. In such a lens, for example, as shown in FIG. 9, only one haptic may be drawn towards lens body 12. It is to be understood that the various embodiments of the invention described and claimed herein may be constructed so that either one or more of the haptics may be demountably coupled to lens body 12.

As shown in FIGS. 9 and 10, groove 48 is formed of a size and shape to complement the size and shape of loop 18, so that loop 18 will be firmly, yet removably, held in groove 48. As shown, loop 18 is substantially circular, although other shapes may be used as is well-known in the art. Thus, in order to complement the shape of loop 18 groove 48 and ridge 50 are substantially semi-circular. In use, loop 18 is placed in groove 48 so that ridge 50 projects through aperture 19, thus holding loop 18 to lens body 12 and bending haptic 14 towards lens body 12, as shown in dotted outline, to create a more compact lens which is easier and safer to insert.

Figure 12:
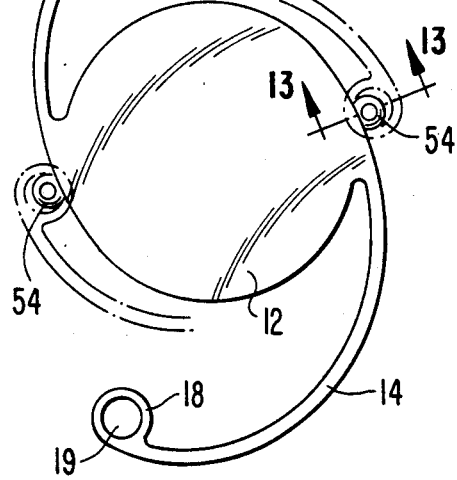
FIG. 12 is a plan view of another embodiment of the invention.
Figure 13:
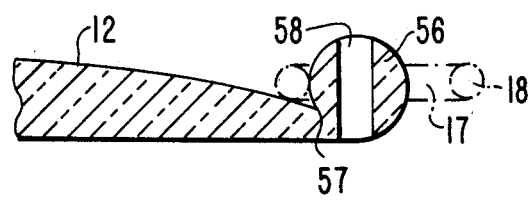
FIG. 13 is a sectional view along line 13—13 of FIG. 12.

FIGS. 12 and 13 show another embodiment of the invention. The typical intraocular lens is approximately 6.0–7.0 mm. in diameter. Forcep holes in the lens body to help manipulate the lens, attaching means as herein described fixed to the lens body, or other elements fixed to the lens body remove approximately 1.0 mm. of effective visual diameter. Thus, the patient only uses approximately 5.0–6.0 mm. of the lens for seeing.

In the lens shown in FIG. 12, lens body 12 is a diameter equal to the effective visual diameter of an intraocular lens, i.e., approximately 5.0–6.0 mm. This provides for a compact overall lens design which is easier to manipulate in the small eye chamber. The visual performance would be identical to lenses of conventional size. However, in order to manipulate lens 10 and in accordance with the present invention to provide attaching means for the haptics, projections 54 or "ears" are provided projecting from the peripheral edge of lens body 12. Preferably projections 54 are integrally formed with lens body 12, although they could be a separate element fixed to lens body 12.

Projections 54 may assume any shape to complement loop 18. As shown, loop 18 and projections 54 are substantially circular. Projection 54 includes a bulbous ridge 56 which forms a groove 57 adjacent the sloping shoulder of lens body 12. A manipulation aperture 58, as is well-known in the art, may also be included in projection 54. In use, ridge 56 projects through aperture 19 of loop 18 to retain loop 18 against lens body 12. Thus, in this embodiment, a highly compact lens has been provided which significantly facilitates lens insertion.

Figure 14:
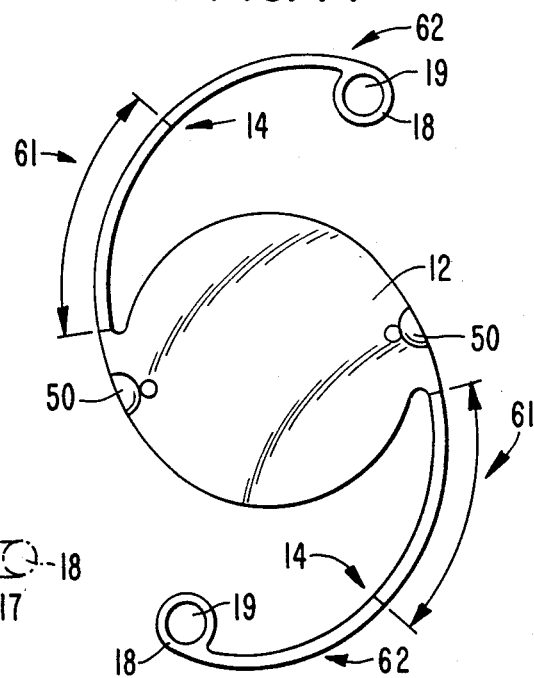
FIG. 14 is a plan view of another embodiment of the invention.

FIG. 14 shows another embodiment of the present invention. In this embodiment, haptics 14 are formed in at least two parts, which may or may not be integral, depending on the particular lens construction. As shown the parts are integrally formed. A first, inner part 61 of haptic 14 is formed of a flexible material, such as Prolene. A second, outer part 62 is formed from a material different from the first part material, which is non-irritating to the eye, such as PMMA. Thus, the haptics are provided with the flexibility and resiliency of Prolene and with the non-irritating qualities of PMMA. It is within the scope of the present invention to construct the haptics of more than two different materials in order to obtain particular haptic characteristics. Although FIG. 14 shows the two-part haptics in the context of the embodiment shown in FIG. 10, it is to be understood that the multi-part haptic structure of the present invention could have applicability to other lens structures, including one, two, or multiple piece lens, and lenses with or without any particular snag-resistant element at the end of the haptics.

Figure 15:
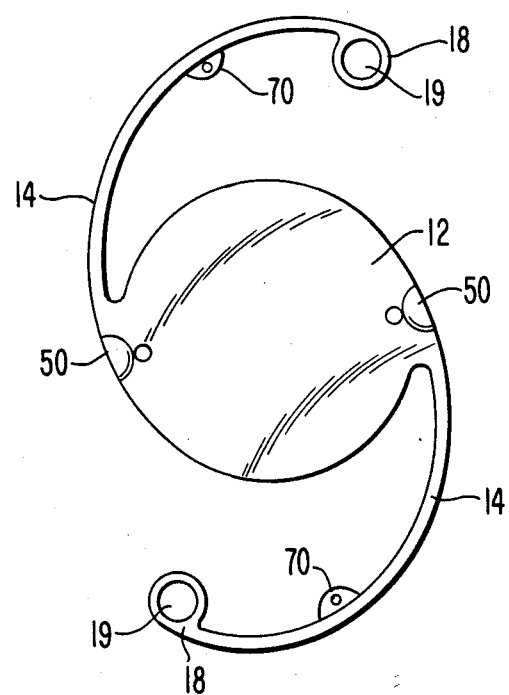
FIG. 15 is a plan view of another embodiment of the invention.

As shown in FIG. 15, haptics 14 may be formed with an intermediate maneuvering hole 70 as is well-known in the art. Although FIG. 15 shows maneuvering hole 70 in the context of the embodiment of FIG. 10, it is to be understood that maneuvering hole 70 may be used with any embodiment described herein or within the scope of the following claims. Also, maneuvering hole may be integrally molded into haptic 14, as shown, or may be formed in any other manner, such as by twisting the haptic in coil fashion.

Manuevering hole 70 allows the surgeon to exercise greater control over the haptic when it is released from the lens body attachment element. This ensures that the haptic will not spring from the lens and injure delicate eye tissue. When releasing the haptic, the surgeon merely grasps maneuvering hole 70 with a forcep to control its release from the attaching means.

While preferred embodiments of the present invention have been illustrated and described, it is to be understood that these are capable of variation, particularly in matters of size, shape and arrangement of parts, within the scope of this invention. The invention should be interpreted according to the broad general meaning of the terms in which the appended claims are expressed.

I claim:

1. An easily insertable intraocular lens comprising: a lens body having an optical portion; at least one flexible positioning and supporting element extending radially outwardly from the periphery of said lens body and terminating in a free end; snag-resistant means integrally formed on said free end of said element for smoothly guiding and positioning the lens across eye tissue during insertion of the lens, said snag-resistant means comprising a continuous, smoothly curved open loop; and lens body attachment means disposed on said lens body for demountably coupling said snag-resistant means of said positioning and supporting element to said lens body during insertion of the lens into the eye so that the radial extent of said positioning and supporting element is reduced to provide easy insertion, said lens body attachment means comprising a button element, said button element having snag-resistant sloping shoulders and a groove cut into said shoulders, and wherein an inner edge of said open loop fits within said groove for demountably coupling said snag-resistant means to said lens body during insertion of the lens into the eye.

2. An easily insertable intraocular lens comprising: a lens body having an optical portion; at least one flexible positioning and supporting element extending radially outwardly from the periphery of said lens body and terminating in a free end; snag-resistant means integrally formed on said free end of said element for smoothly guiding and positioning the lens across eye tissue during insertion of the lens, said snag-resistant means comprising a continuous, smoothly curved open loop; and lens body attachment means disposed on said lens body for demountably coupling said snag-resistant means of said positioning and supporting element to said lens body during insertion of the lens into the eye so that the radial extent of said positioning and supporting element is reduced to provide easy insertion, said lens body attachment means comprising a flange having a curved outer end wherein said flange fits within said open loop to demountably couple said snag-resistant means to said lens body.

3. An easily insertable intraocular lens comprising: a lens body having an optical portion and at least one shallow well in said lens body; at least one flexible positioning and supporting element extending radially outwardly from the periphery of said lens body and terminating in a free end; snag-resistant means integrally formed on said free end of said element for smoothly guiding and positioning the lens across eye tissue during insertion of the lens, said snag-resistant means compirising a continuous, smoothly curved open loop; and lens body attachment means disposed on said lens body for demountably coupling said snag-resistant means of said positioning and supporting element to said lens body during insertion of the lens into the eye so that the radial extent of said positioning and supporting element is reduced to provide easy insertion, said lens body attachment means comprising a button element disposed in said well wherein said button element fits within said open loop to demountably couple said snag-resistant means to said lens body.

4. An easily insertable intraocular lens comprising; a lens body having an optical portion; at least one flexible positioning and supporting element extending radially outwardly from the periphery of said lens body and terminating in a free end; snag-resistant means integrally formed on said free end of said element for smoothly guiding and positioning the lens across eye tissue during insertion of the lens; lens body attachment means disposed on said lens body for demountably coupling said snag-resistant means of said positioning and supporting element to said lens body during insertion of the lens into the dye so that the radial extent of said positioning and supporting element is reduced to provide easy insertion, said lens body attachment means comprising a flange with a curved outer end; and second attachment means on said snag-resistant means for removably connecting to said lens body attachment means, said second attachment means comprising a flange with a curved outer end which is shaped to complement said lens body attachment means.

5. An intraocular lens comprising; a lens body having an optical portion; at least one spaced flexible positioning and supporting elements extending radially outwardly from the periphery of said lens body; at least one flange with a curved outer end forming a first hook portion disposed on said lens body; and at least one flange with a curved outer end forming a second hook portion complementary in size and shape to said first hook portion disposed on said positioning and supporting element so that said flanges may be demountably coupled during insertion of the lens into the eye so that the radial extent of said positioning and supporting elements is reduced to provide easy insertion.

* * * * *